(12) United States Patent
Boos

(10) Patent No.: US 10,856,887 B2
(45) Date of Patent: Dec. 8, 2020

(54) SURGERY DEVICE FOR PERFORMING SURGERY ON THE HUMAN KNEE

(71) Applicant: Carsten Boos, Goldach (CH)

(72) Inventor: Carsten Boos, Goldach (CH)

( * ) Notice: Subject to any disclaimer, the term of this patent is extended or adjusted under 35 U.S.C. 154(b) by 126 days.

(21) Appl. No.: 16/085,495

(22) PCT Filed: Mar. 9, 2017

(86) PCT No.: PCT/EP2017/055598
§ 371 (c)(1),
(2) Date: Sep. 14, 2018

(87) PCT Pub. No.: WO2017/157767
PCT Pub. Date: Sep. 21, 2017

(65) Prior Publication Data
US 2019/0083107 A1 Mar. 21, 2019

(30) Foreign Application Priority Data
Mar. 16, 2016 (DE) .................. 10 2016 204 307

(51) Int. Cl.
| | |
|---|---|
| A61B 17/15 | (2006.01) |
| A61B 17/66 | (2006.01) |
| A61F 2/46 | (2006.01) |
| A61B 17/02 | (2006.01) |
| A61B 17/16 | (2006.01) |
| A61B 90/00 | (2016.01) |

(52) U.S. Cl.
CPC .......... *A61B 17/155* (2013.01); *A61B 17/025* (2013.01); *A61B 17/154* (2013.01);
(Continued)

(58) Field of Classification Search
CPC .......... A61B 17/025; A61B 2017/0268; A61B 17/154; A61B 17/155; A61B 17/1764;
(Continued)

(56) References Cited

U.S. PATENT DOCUMENTS

| | | | |
|---|---|---|---|
| 5,662,656 A * | 9/1997 | White | ................ A61B 17/155 606/86 R |
| 5,911,723 A | 6/1999 | Ashby et al. | |

(Continued)

FOREIGN PATENT DOCUMENTS

| | | |
|---|---|---|
| EP | 0809969 A2 | 12/1997 |
| EP | 1348382 A2 | 10/2003 |

(Continued)

*Primary Examiner* — Larry E Waggle, Jr.
(74) *Attorney, Agent, or Firm* — Seed Intellectual Property Law Group LLP

(57) ABSTRACT

A surgery device for operating on the human knee. The surgery device comprises a guide component and a tensioning component. The guide component comprises a base body having a base surface for disposing on a tibial end face and comprises guide elements extending from the base surface. The tensioning component is set up for tensioning the guide component such that the ligaments of the knee are uniformly tensioned in the flexed state of the knee. A truing and drilling component for truing and drilling a femoral end face can be pushed onto the guide elements and fixed at various positions relative to the base surface. The risk of injury and misuse during the surgery on a human knee is reduced and the duration of surgery is shortened by means of the surgery device according to the invention.

19 Claims, 13 Drawing Sheets

(52) U.S. Cl.
CPC .......... *A61B 17/1675* (2013.01); *A61B 17/66* (2013.01); *A61F 2/468* (2013.01); *A61B 2017/0268* (2013.01); *A61B 2090/061* (2016.02)

(58) Field of Classification Search
CPC .............. A61B 17/56; A61B 2017/564; A61B 2017/567; A61B 17/66; A61F 2/46; A61F 2/461; A61F 2/4657; A61F 2002/4658; A61F 2/468; A61F 2/4684
See application file for complete search history.

(56) References Cited

U.S. PATENT DOCUMENTS

| | | | |
|---|---|---|---|
| 6,056,756 A * | 5/2000 | Eng | A61B 17/155 606/87 |
| 6,758,850 B2 | 7/2004 | Smith et al. | |
| 8,734,453 B2 * | 5/2014 | Tuttle | A61B 17/164 606/87 |
| 9,138,332 B2 | 9/2015 | Harris et al. | |
| 10,357,255 B2 * | 7/2019 | Collazo | A61B 17/142 |
| 2005/0256527 A1 | 11/2005 | Delfosse et al. | |
| 2006/0189998 A1 | 8/2006 | Rasmussen | |
| 2007/0293868 A1 | 12/2007 | Delfosse et al. | |
| 2012/0259342 A1 | 10/2012 | Chana et al. | |
| 2015/0209158 A1 * | 7/2015 | Reeve | A61F 2/4684 623/20.35 |

FOREIGN PATENT DOCUMENTS

| | | |
|---|---|---|
| GB | 2526724 A | 12/2015 |
| WO | 2006042743 A2 | 4/2006 |
| WO | 2011135372 A1 | 11/2011 |

* cited by examiner

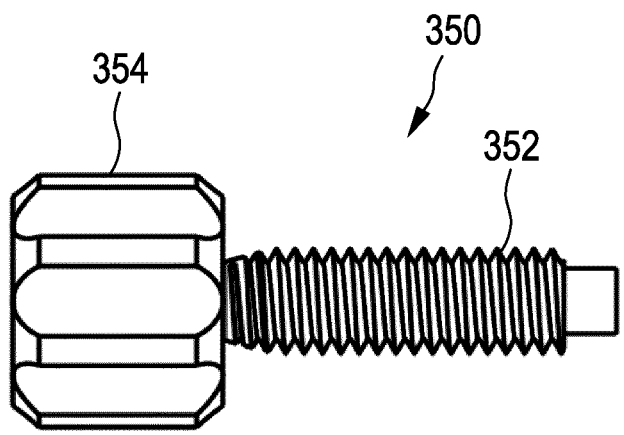
FIG. 7a
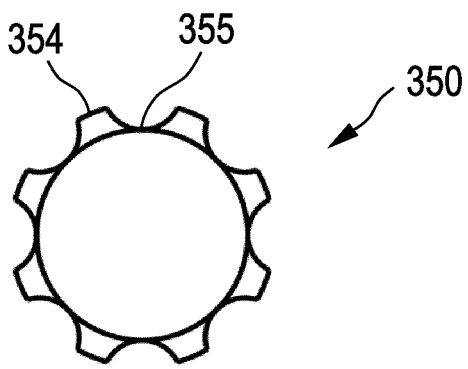
FIG. 7b
FIG. 8
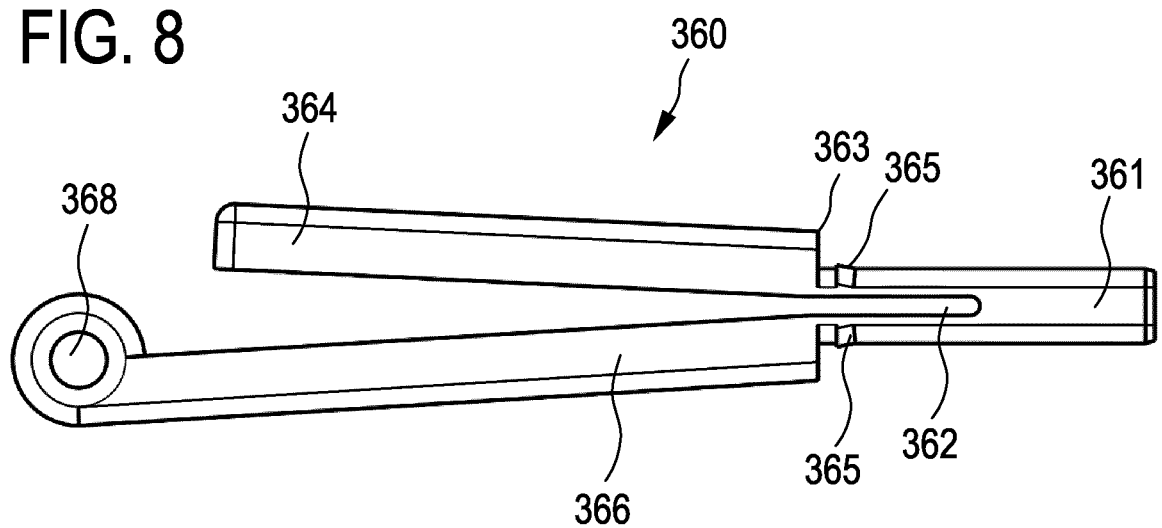

SURGERY DEVICE FOR PERFORMING SURGERY ON THE HUMAN KNEE

BACKGROUND

Technical Field

The present invention relates to a surgery device. The present invention particularly relates to a surgery device used for performing surgery on a human knee, particularly for implanting a knee endoprosthesis.

Description of the Related Art

The human knee joint allows motion between the thigh bone (femur) and lower leg bones, namely the calf bone (fibula) and shin bone (tibia). At the front side of the knee joint, the kneecap (patella) is another joint structure. Disparities in the joint surfaces between the femur and tibia are compensated for by cartilage discs, known as menisci. If the knee is severely degraded, a condition known as knee joint arthritis, or if the knee is injured, complete prosthesis of the knee joint may become necessary.

The knee joint is stabilized in the lateral direction by its two side bands, namely one inner and one outer band, known as ligaments, to prevent buckling into a bowlegged or knock-kneed position of the legs. The anterior and posterior cruciate ligaments in the middle of the knee joint limit the displacement of the femur and tibia in the sagittal plane.

A knee endoprosthesis typically comprises two metal components cemented or anchored without cement in the femur and the tibia, and a sliding component between said components, particularly made of polyethylene. A plurality of methods are known for the rotating and sliding mechanism.

Various operational techniques are described for implanting a knee endoprosthesis. As a rule, the ends of the femur and tibia are first sawn off and smoothed. Any preexisting axial malalignment (bowlegged or knock-kneed) should be corrected by applying the correct ligament tension. Once the ends have been prepared, the definitive femur rotation is prepared either by anatomically orienting, ligament balancing, or a combination. For the ligament-balancing method, the ligaments are uniformly tensioned using various tensioning devices in the flexed (and sometimes also extended) state of the knee, and the position of the device to be subsequently inserted is defined by means of drilling templates present in the tensioning device. This surgery step does not achieve correct rotation of the femur prosthesis, but for correctly determining the size of the femur component in the sagittal and frontal place (and the tibia component must also be adapted to size in parallel thereto), in an additional step after removing the tensioning device, a gauge block allowing truing of the cutting planes at the top and bottom sides of the femur must be attached to the end of the femur by means of the previously prepared holes. The top and bottom sides of the femur are then gauged and, if necessary, measured, at an angle to the end face of the femur.

The term truing designates visually inspecting and measuring the top and front side of the femur, optionally comprising measuring by means of a feeler gauge, such as a sheet-metal feeler gauge.

The gauge block is subsequently removed and, depending on the size of the prosthesis, various prosthetic drilling templates are placed separately on a cutting block. The holes are drilled and the device(s) removed. A cutting block, not shown, is separately placed in the drilled holes. Using further prosthetic drilling templates, the two final holes are made for the femur prosthesis.

Tensioning the tensioning device, including providing the auxiliary holes, followed by attaching the gauge block and truing the cutting planes, then applying the prosthetic drilling template, requires three devices, each of which is difficult and error-prone to install and remove. Correctly operating the devices requires a high level of experience, which can cause problems particularly for young, inexperienced surgeons. Working with a plurality of devices is also time-intensive, which makes the surgery more expensive overall, and increases the risks of the surgery and of infection.

The bone cutting guide unit of EP 0 809 969 B1 is known from the prior art, for example. The tensioning device is inserted when the knee is in an extended state, as shown in FIG. 6, and auxiliary holes 54 are provided in the femur, but not in the end face of the femur. After removing the device, as shown in FIGS. 7 and 9, for example, a size of the prosthesis is then determined in a plurality of steps. Drilling the mounting holes is then possible after again placing the device, as shown in FIG. 16. The large number of steps required for the surgery process and the complex execution of the surgery lead to a time-intensive, expensive, and high-risk surgery. The forced position forced by the tissue engagement surfaces 3 and 6 further causes tensioning of the ligaments and greater potential for error in comparison with torque-balanced alignment of the femur.

A device for adjusting the flexed distance of a knee prosthesis is known from EP 1 348 382 B1. The instrument comprises a base part designed for arranging relative to the proximal end of the shin bone, a plate protruding from the base part and designed to be horizontal relative to the distal end of the thigh when the base part is disposed relative to the shin bone, and comprises markings on the plate for defining a gap measurement. The plate is part of a protruding region of an I-beam protruding from the base part. Said instrument requires selecting a suitable cutting block by testing before the holes for the cutting block can be set, also making the surgery time-intensive and error-prone.

BRIEF SUMMARY

Provided is a device for performing surgery on knee endoprostheses and improving the safety of executing the surgery.

Provided is a surgery device for performing surgery on a human knee, wherein the surgery device comprises a guide component, a tensioning component, and a truing and drilling component. The guide component comprises a base body having a base surface for disposing on a tibial end face and guide elements extending from the base surface. The tensioning component is set up for tensioning the guide component such that the ligaments of the knee are uniformly tensioned in the flexed state of the knee. A truing and drilling component for truing and drilling the femoral end face can be pushed onto the guide elements. The truing and drilling component is can be fixed in various positions relative to the base surface.

The surgery device is then put to use during the surgery when the femoral end face and the tibial end face have been prepared. The surgery device is inserted into the flexed knee, wherein the base surface of the base body makes contact with the tibial end face. The guide elements extending from the base surface then run parallel to the femoral end face and are set up for being aligned to the same. Because the truing and drilling component can be pushed onto the guide element, incorrect positioning of the previously used gauge block is not possible. The intermediate step of releasing the tensioning device and removing the tensioning device is also eliminated, whereby the complexity of the surgery is reduced. Complications for the patient can thereby be minimized by shortening the surgery time.

The surgery device is accordingly set up such that truing and drilling the femur is possible without releasing the tensioning device. The surgery method is thus simplified, as fewer devices are used.

Because the truing and drilling component can be pushed onto the guide elements, the femoral end face can be trued without releasing the tensioning component and the guide component or removing said components from the femur. The truing and drilling can thus be performed with little effort and reduced risk of error.

Because the truing and drilling component can be fixed at different positions relative to the base surface, the truing and drilling component can be used universally, mostly independently of the size of the knee.

The end face of the femur and tibia are the surfaces opposite each other in the knee joint. The front or top sides of each of the bones refer to those sides on the side of the patella in the knee joint. In other words, the side typically referred to as the front for a person. The back sides of the femur and the tibia are thus those sides adjacent to the hollow of the knee.

The problem that a surgeon must first determine the size of the prosthesis and the location of additional saw cuts before the prosthesis holes are drilled in the femur is thereby solved. The truing and drilling component can be used for truing and drilling by means of a single truing fixture placed on the guide elements and fixed in place.

In one embodiment, the tensioning component comprises a tensioning cylinder and a tensioning lever. The tensioning cylinder is guided by the guide elements along a longitudinal axis of the tensioning cylinder, and the tensioning lever is set up for tensioning the tensioning cylinder relative to the base body.

The tensioning component thus preferably allows the surgery device to be tensioned at a defined distance between the tensioning cylinder and the guide component or base body. For example, the tensioning cylinder can be fixed relative to the femur and the base body can be displaced in the direction of the tibial end face until the desired tension is achieved. Uniform tensioning of the ligaments of the knee can particularly be thus ensured. The tensioning cylinder is preferably guided by the guide elements along a longitudinal axis of the tensioning cylinder and the guide elements ensure that the truing and drilling components can be displaced.

In one embodiment, the tensioning cylinder at least partially comprises a latching profile having a plurality of latching positions on a cylindrical surface thereof set up such that a corresponding latching element of the tensioning lever can engage at a plurality of heights of the tensioning cylinder relative to the base body.

In one embodiment, the latching profile and the corresponding latching element are set up such that increasing the distance of the tensioning cylinder from the base body is made possible and reducing the distance of the tensioning cylinder from the base body is blocked.

The tensioning cylinder thus preferably latches at a plurality of positions relative to the tensioning lever and the base body. Because the distance of the tensioning cylinder from the base body can only be increased, but not decreased, undesired releasing of the tensioning component is prevented.

In one embodiment, the tensioning cylinder comprises a cutout in the longitudinal direction. The cutout can particularly be implemented in the longitudinal direction as a through hole in the longitudinal direction. Because the tensioning cylinder is designed for having a cutout in the longitudinal direction, particularly in the form of any sort of recess, or for having a through hole in the longitudinal direction, jamming due to bodily tissues or fluids can be prevented. Complications in the surgery can thus be further avoided.

In one embodiment, the tensioning cylinder comprises one or more through holes perpendicular to the longitudinal direction.

The through holes are preferably designed for allowing the tensioning cylinder to be attached and tensioned on the femur by means of a mounting element. The mounting element can, for example, be implemented in the form of a T-mount, allowing simple insertion and removal of the mounting element from the femur. The center of the T-mount is the center of rotation (pivot bearing) ensuring uniform ligament tension on the right and left by means of torque balancing.

The tensioning cylinder preferably comprises three through holes perpendicular to the longitudinal direction for implementing different sizes. For example, the center through hole can be designed for an average knee size, while through holes closer to or further from the base body in the direction of the cylinder are implemented for larger or smaller knees. The usability of the surgery device across a wide range is thereby ensured.

In one embodiment, the tensioning lever comprises a first arm and a second arm having an intermediate pivot point. The first arm, the second arm, and the intermediate pivot point are set up such that the second arm can be tensioned against the tensioning cylinder by pretensioning the first arm.

In one embodiment, the tensioning component further comprises a mounting element. The tensioning lever can be attached to the base body of the guide component at the pivot point thereof. The tensioning component is preferably implemented in the form of a screw, wherein a corresponding thread is provided in the base body. The tensioning lever is thus only rotationally displaceable relative to the base body, wherein tension results from a relative displacement of the tensioning lever or the base body and the tensioning cylinder.

In one embodiment, the tensioning component further comprises a tensioning spring set up for tensioning the first arm relative to the base body. The tensioning spring particularly tensions the first arm relative to the base body, such that the second arm rotationally supported by the pivot point is tensioned against the tensioning cylinder.

In one embodiment, the base body comprises a cutout in the base surface for receiving the tensioning lever. Because the tensioning lever can be inserted into the base body by means of a cutout in the base surface, it is possible to separate the tensioning lever completely from the base body after use. Thorough disinfection and reusability is thereby ensured.

In one embodiment, the base body comprises an opening for actuating the tensioning lever on a side surface thereof. The tensioning lever can particularly be actuated in opposition to the pretension, whereby the second arm is also released from the pretension by means of the pivot point. Releasing of the tensioning component is thus possible by actuating the tensioning lever. As an example, the tensioning lever is actuated by pressing the first arm against the tensioning spring.

In one embodiment, the guide component comprises two guide elements spaced apart from each other and extending in the same direction from the base body. The two guide elements each comprise an inner lateral surface facing towards the other guide element, and an outer surface opposite the inner lateral surface.

The guide elements can thus provide two guides, one on the opposite inner lateral surfaces and one on the outer lateral surfaces. The inner lateral surfaces are preferably implemented for guiding the tensioning cylinder and the outer lateral surfaces for guiding a truing and drilling component.

In one embodiment, each of the inner lateral surfaces has a concave cylindrical shape, such that the two inner lateral surfaces define a cylindrical guide as the space between said surfaces. A cylindrical guide particularly for the tensioning cylinder is advantageously thereby defined. The guide allows the tensioning cylinder to be rotatable about the cylindrical axis. One of the side walls of the guide elements preferably comprises a penetration through which the tensioning lever extends from the bottom side of the base body. Because the tensioning cylinder having the latching element is placed on the side at which the penetration is provided, the tensioning element can be tensioned in the guide relative to the tensioning lever.

In one embodiment, a spacing between the inner lateral surfaces on a front side of the base body is different from a spacing between the lateral surfaces on a back side.

A protrusion sized to fit only through the larger of the openings can also be provided on the tensioning cylinder. Incorrect placement, for example by rotating the tensioning cylinder 180° about the axis thereof, is thus not possible. In other words, it is possible to place the tensioning cylinder only in the correct orientation. In other embodiments, the tensioning cylinder can also be implemented such that said cylinder can be place in two orientations relative to the longitudinal axis thereof.

In one embodiment, one of the outer surfaces comprises a recess in the direction of extent of the guide elements, and the other of the outer surfaces comprises a protrusion for guiding a truing and drilling component. Because one of the surfaces comprises a recess and the other of the surfaces comprises a protrusion, the truing and drilling component cannot be placed when incorrectly rotated by 180° relative to the guide elements. Incorrect operation of the surgery device is thus avoided. The guide elements thus define a linear guide on the outer surfaces thereof for the truing and drilling component, allowing no relative rotation.

In one embodiment, the guide elements extend in a front region of the base body and a radius of the base body corresponds to the tibial base surface. An average tibial surface is preferably assumed and the base surface of the base body corresponds to the average tibial surface. The shape of the tibial surface is known. In other embodiments, two or more different base surfaces can be provided for tibial sizes deviating severely from the average.

In one embodiment, the radius of the base body transitions into the radius of the truing and drilling component. Risks of injury or misuse due to edges or protruding corners are thus particularly eliminated.

In one embodiment, the truing and drilling component comprises a gauge fixture, wherein the gauge fixture comprises at least one groove for an upper femoral cut.

Because the gauge fixture comprises a groove for an upper femoral cut, the upper femoral cut can be trued by means of the gauge fixture.

In one embodiment, the truing and drilling component comprises attachment means set up for fixing the position of the gauge fixture relative to the guide component.

When the guide component is tensioned between the femur and tibia relative to the tensioning component, the size of the prosthesis to be inserted later can be determined by means of the truing and drilling component. When the gauge fixture is at the correct position relative to the guide component and thus relative to the femur, the position can be fixed by means of the attaching means. Reliable truing of the upper femoral cut and reliable drilling of the prosthesis holes can thus be enabled.

In one embodiment, the attaching means is implemented in the form of an adjusting screw and the gauge fixture comprises a thread corresponding to the adjusting screw. The thread corresponding to the adjusting screw is present on a lateral outer surface of the gauge fixture in one embodiment and extends through the gauge fixture to the guide element. Tightening the adjusting screw can thus fix the position of the gauge fixture relative to the guide component.

In one embodiment, the fastening means is disposed on a front side of the truing and drilling component. The front side of the truing and drilling component is the side facing away from the femoral end face, that is, toward the surgeon.

The arrangement on the front side allows use of the attaching means for surgery on the left as well as the right knee, without ligaments at the sides of the truing and drilling component preventing the fastening means from being disposed.

In one embodiment, the fastening means is implemented in the form of a locking pin. The gauge fixture comprises at least one pass-through opening and a guide element comprises at least one associated cutout. The locking pin can be inserted into the cutout through the pass-through opening and the position of the gauge fixture relative to the guide element can thereby be fixed. In comparison with the adjusting screw, the locking pin can be used for fixing only at predefined positions of the guide element.

In one embodiment, the at least one pass-through opening and the at least one associated cutout are rectangular in design. Secure retention of the locking pin in the pass-through opening and the associated cutout can thereby be obtained, because the locking pin is secured against rotating.

In one embodiment, the gauge fixture comprises a plurality of pass-through openings and the guide element comprises a plurality of associated cutouts, wherein pass-through openings and cutouts associated with each other have the same orientation. The distances of the pass-through openings from the base body preferably differ from the distances of the gauge fixture, so that fixing in different pass-through openings by means of the locking pin defines different positions of the gauge fixture relative to the base body.

In one embodiment, pass-through openings different from each other have different orientations. It is thereby possible that a particular orientation defines a particular position of the gauge fixture relative to the guide element. In other words, incorrect or undesired positioning of the gauge fixture can be prevented in that a particular position corresponds to a particular orientation. The pass-through openings different from each other preferably have orientations different from each other by 30° each, particularly preferably by at least 45° each.

In one embodiment, the gauge fixture comprises an arched shape and is guided by outer surfaces of two guide elements. In other words, the gauge fixture is preferably pushed onto the guide elements laterally. Guiding by the outer surfaces of the two guide elements preferably differs thereby between the guide elements, in that, for example, a groove is provided in one outer surface and a protrusion in the other. The gauge fixture can thus be prevented from being placed in the incorrect orientation. At least one, particularly both of the guides defined on the outer surfaces are preferably implemented as dovetail guides.

In one embodiment, the gauge fixture comprises at least one groove for truing a lower femoral cut. Because the gauge fixture comprises a groove for a lower femoral cut, no additional gauge fixture is necessary for truing the lower femoral side. This reduces complexity during the surgery and prevents the eliminated, additional gauge fixture from being applied incorrectly.

In one embodiment, the cutting planes for the upper femoral cut and the lower femoral cut are not parallel. The upper cutting plane particularly encloses a cutting angle of 95° to the femoral end face. The orientations of the cutting planes for the upper femoral cut and the lower femoral cut are thereby particularly implemented according to the requirements of the prosthesis. In other embodiments, the cutting planes can also enclose other angles to the femoral end face. Furthermore, in other embodiments, further cutting planes, such as diagonal cutting planes, can also be made possible by the gauge fixture. This makes it possible for the gauge fixture to be compatible with a plurality of prostheses, whereby the applicability of the surgery device is improved.

In one embodiment, the gauge fixture comprises two drill bushings for drilling the femoral prosthesis holes. The drill bushings are preferably symmetrical and each disposed in one arm of the arch-shaped gauge fixture. The position of the drill bushings corresponds to the final drill position of the femoral prosthetic element. In one embodiment, the drill bushings are integrated in the gauge fixture. In the present embodiment, the gauge fixture thus comprises a material of sufficient hardness. In another embodiment, the drill bushings are implemented as drill bushing inserts, particularly thus clamped or pressed into the gauge fixture.

In one embodiment, the gauge fixture comprises a millimeter scale on the front side thereof. The millimeter scale is referenced by a marking on the guide component. The millimeter scale enables a surgeon to position the surgery device, particularly the gauge fixture, precisely at intermediate distances not able to be locked by means of the locking pin.

Provided is a use of a surgery device according to the invention for performing surgery on the human knee, particularly for implanting a knee endoprosthesis.

BRIEF DESCRIPTION OF THE SEVERAL VIEWS OF THE DRAWINGS

Further embodiments and associated advantages are described below with reference to the attached figures.

FIGS. 7a and 7b show schematic examples of two views of an adjusting screw according to one embodiment example, FIG. 8 shows a schematic example of a locking pin according to one embodiment example.

DETAILED DESCRIPTION

Figure 1:
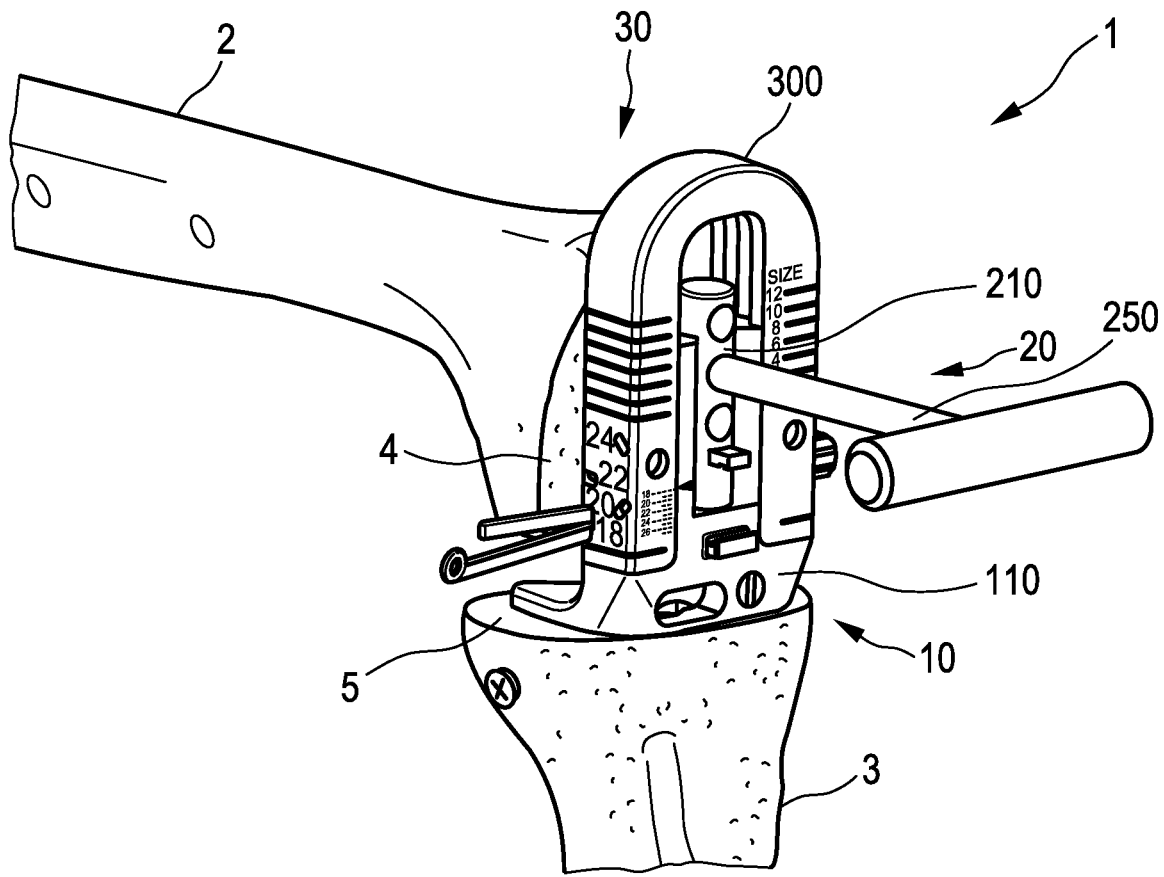
FIG. 1 shows a schematic perspective view of a surgery device according to one embodiment example of the present invention.

FIG. 1 shows an embodiment example of a surgery device 1 as used during a knee surgery in a knee joint. FIG. 1 shows a schematic view of a femur 2 and a tibia 3 disposed at an angle. Before applying the surgery device 1 according to the invention, both a femoral end face 4 and a tibial end face 5 have been prepared for the prosthetic surgery. FIG. 1 shows a schematic view of only the femur 2 and the tibia 3; all further elements of the knee joint are omitted for better visibility.

The surgery device 1 comprises a guide component 10, a tensioning component 20, and a truing and drilling component 30. The surgery device 1 is tensioned between the femur and tibia by the tensioning component 20 such that the ligaments (not shown) are uniformly tensioned. Malpositioning of the prosthesis and consequent malpositioning of the leg is thereby prevented.

The guide component 10 comprises a base body 110 contacting the tibial base surface 5. The tensioning component 20 comprises a tensioning cylinder 210 tensioning the guide component 10 against the tensioning component 20. The tensioning cylinder 210 is fixed on the femoral end face 4 by means of a T-mount 250. Undesired displacing of the tensioning cylinder 210 relative to the femoral base surface 4 can thereby be prevented.

The truing and drilling component 30 comprises a gauge fixture 300 for pushing onto the guide component 10. As can be seen in FIG. 1, the gauge fixture 300 can be pushed onto the surgery device 1, thus enabling truing and drilling of the femur 2 without releasing and removing from the joint the tensioning component 20.

Figure 2:
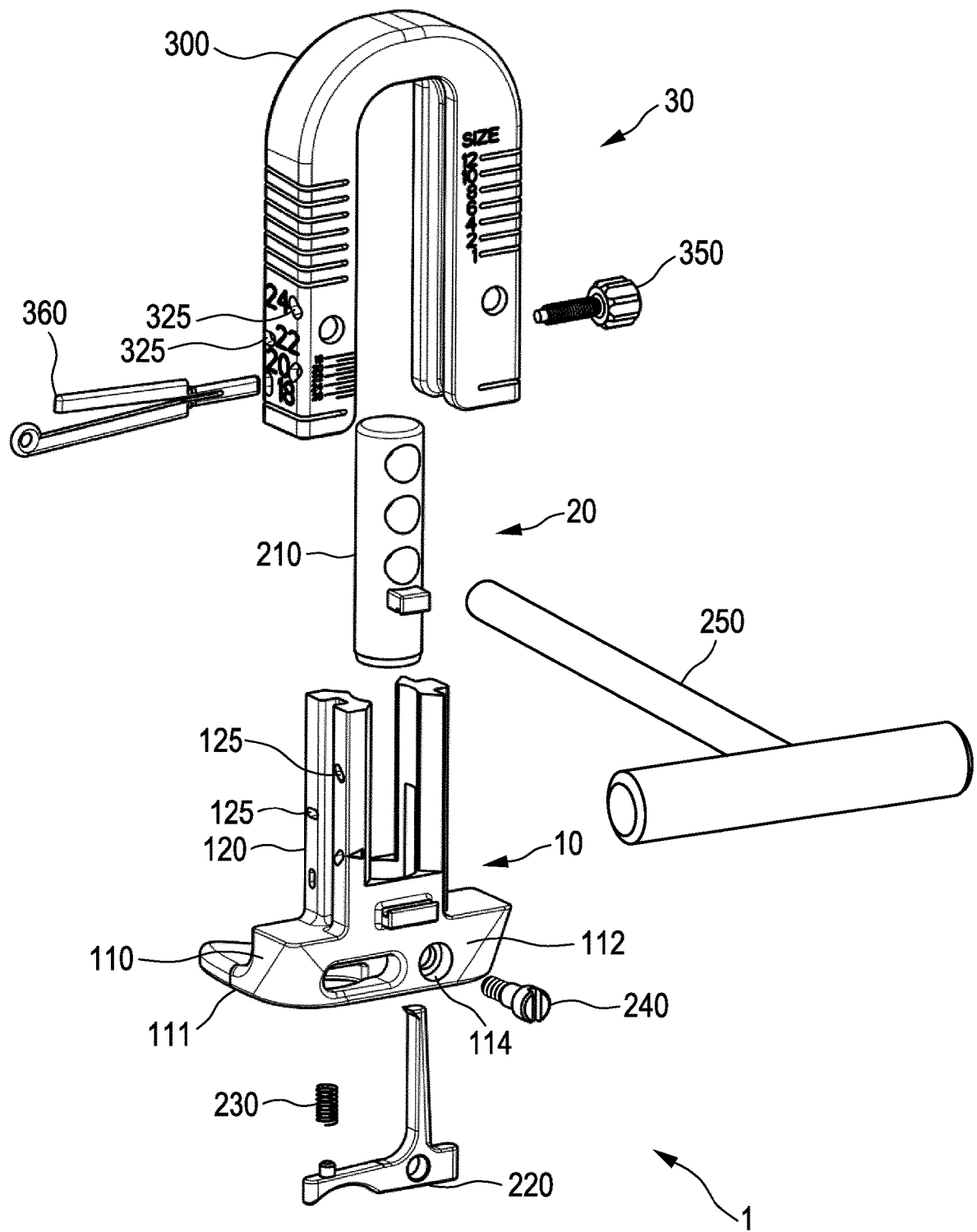
FIG. 2 shows a schematic example explosion view of the surgery device according to one embodiment example of the invention.

FIG. 2 shows the individual components of the surgery device 1 in a schematic exploded view. The guide component 10 comprises a base body 110 and two parallel guide elements 120 extending upward from a base surface 111 of the base body 110. The base surface 111 is set up for contacting the tibial end face. The guide elements 120 are set up for guiding two components, namely the tensioning cylinder 210 on the inner side of the guide elements 120 and the truing and drilling component 30, particularly the gauge fixture 300, on the outer side of the guide elements 120.

The base body 110 comprises various openings set up for receiving various other components of the surgery device 1. The base body 110 has an opening for receiving a tensioning spring 230 on the base surface 111, and a further opening through which a tensioning lever 220 can be inserted through the base body 110 into the guide elements 120. A fastening screw 240 can be inserted through a fastening opening 114 provided on a front surface 112 of the base body 110, by means of which the tensioning lever 220 is rotatably fastened to the guide component 10.

The truing and drilling component 30 comprises the gauge fixture 300 for being fixed at a desired position relative to the guide element 120 by means of an adjusting screw 350 and/or a locking pin 360. The locking pin 360 is inserted through openings 325 in the gauge fixture 300 and placed, for example latched, in corresponding openings 125 on the outer surfaces of the guide elements 120.

Figure 3A:
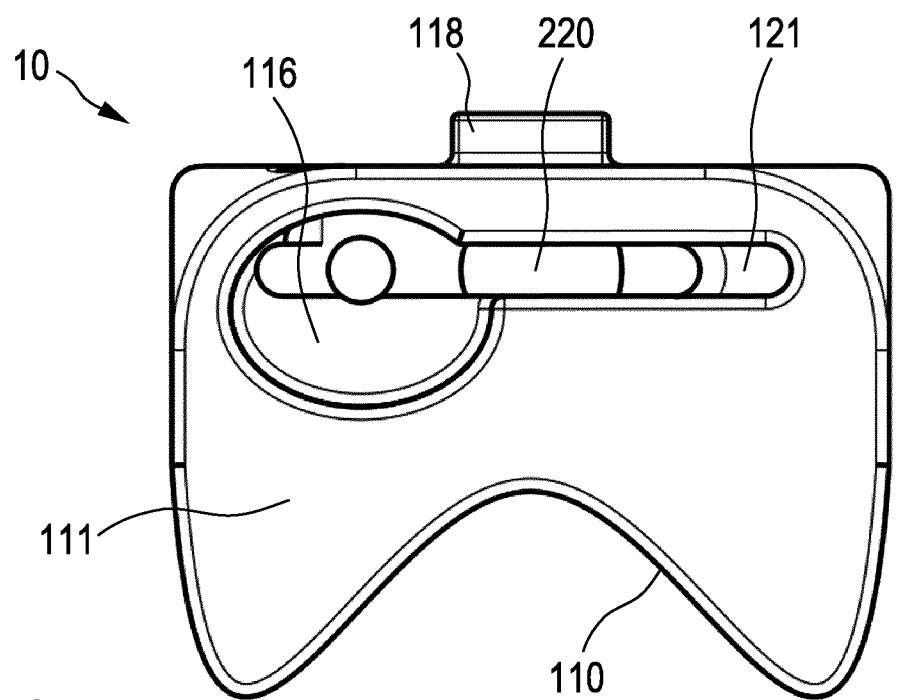
FIGS. 3a-3e show schematic examples of a guide component of a surgery device according to one embodiment example in various views.

The individual components and elements of the surgery device 1 are described below in detail and separately with reference to the further figures. FIGS. 3a to 3e show various views of the guide component 10. FIG. 3a shows a view from below, that is, facing the base surface 111 of the base body 110. The radius of the base surface 111 is adapted to the tibial end face 5 and transitions into that of the gauge fixture 300 at a constantly diminishing radius. Any risk of injury or misuse is thus prevented. FIG. 3a shows an opening 116 into which the tensioning lever 220 is inserted. The tensioning lever 220 extends through a further cutout 121 and through the base body 110 into the guide element 120.

Figure 3B:
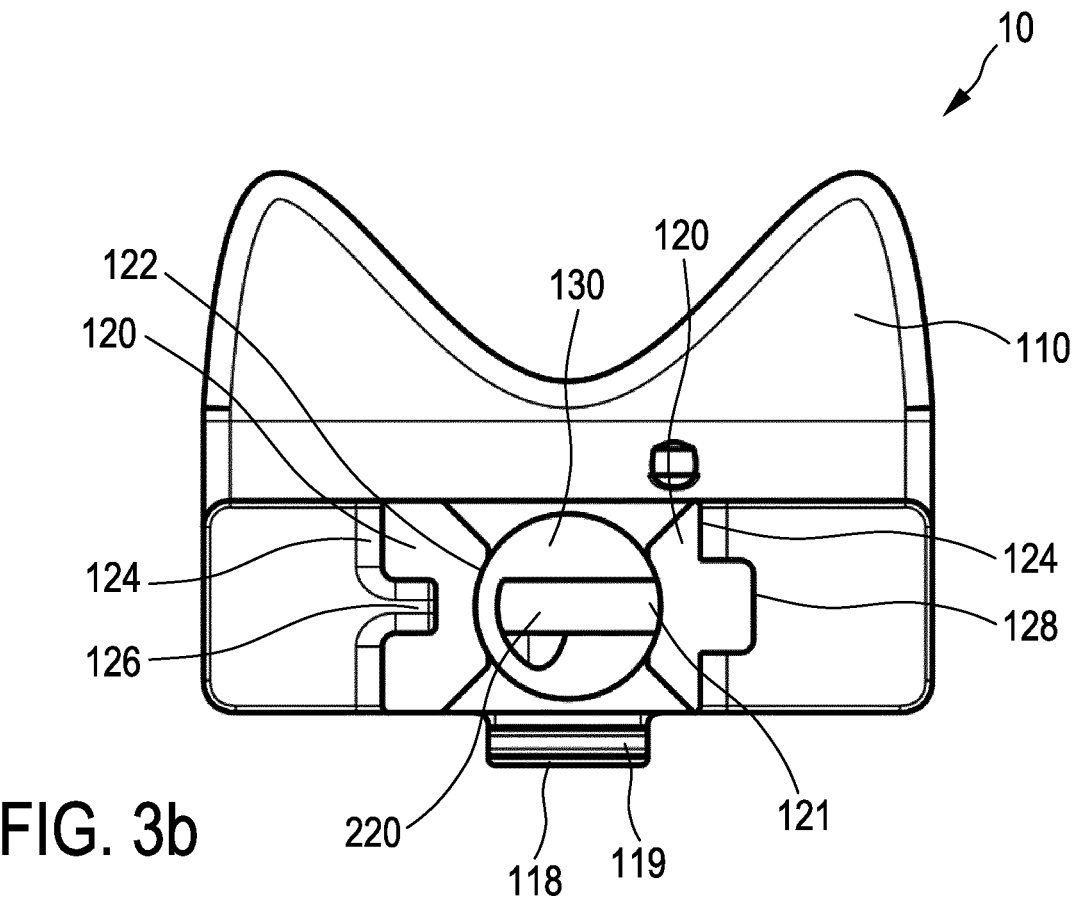

The base body 110 shows a knob 118 on the front side comprising a groove 119 on the top side thereof (cf. e.g. FIG. 3b). The knob 118 and groove 119 form a part of the actual tensioning mechanism. A forceps (not shown) is placed between the knob 118 and a corresponding knob 218 on the tensioning cylinder 210 (cf. FIG. 4) for tensioning. The distance between the base body 110 and the tensioning cylinder 210 is increased by opening the forceps until the desired degree of tension is achieved. In order to prevent the forceps from slipping out of the knob 118 or the knob 218, each of the knobs 118, 218 comprises a corresponding groove 119, 219 on the sides facing toward each other.

The guide component 10 is shown in a view from above in FIG. 3b. A cylindrical guide receptacle 130 is defined between the two guide elements 120. Inner surfaces 122 of each of the guide elements 120 define segments of a cylindrical guide to this end. In the present view, the cutout 121 is also visible, through which the tensioning lever 220 makes contact in the cylindrical guide receptacle 130. FIG. 3b shows further outer surfaces 124 of the guide element 120 forming a second guide for the truing and drilling component 30. To prevent incorrect placing of the truing and drilling component 30 on the guide elements 120, a guide protrusion 128 is implement on the lateral surface 124 show to the left in the drawing, whereas a guide groove 126 is implemented on the lateral surface 124 shown to the right in the drawing.

Figure 3C:
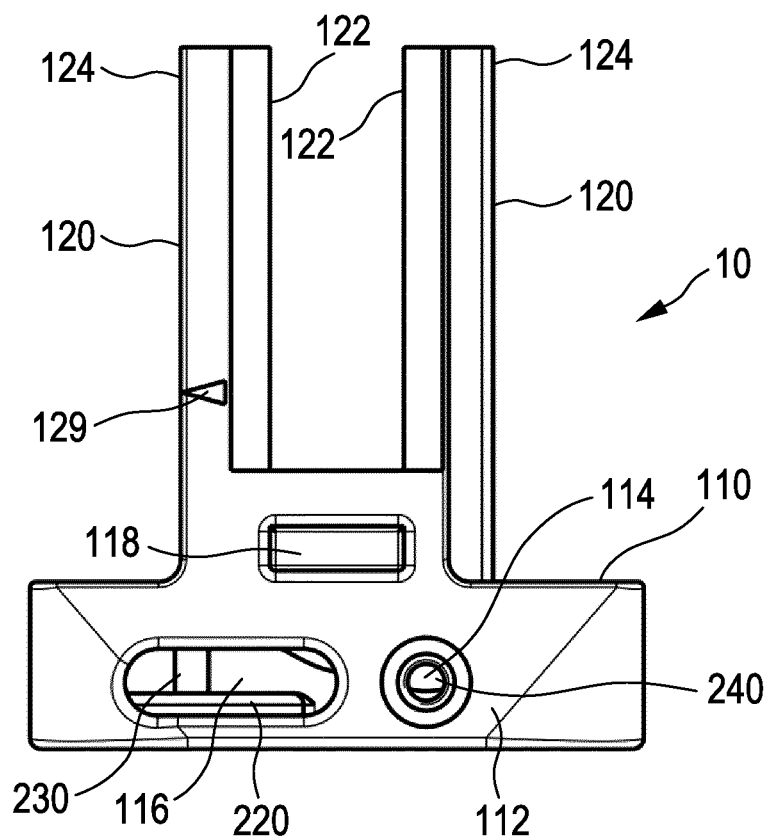

FIG. 3c shows the guide component 10 from above. The front surface 112 comprises the fastening opening 114 into which the fastening screw 240 is inserted. The opening 116 allowing access to the tensioning lever 220 is further identifiable. The tensioning lever 220 can be pressed against the tensioning spring 230 by means of the opening 116 and a tension of the tensioning lever can thereby be released. An indicator 129 is shown on the front side of the guide element 120. The indicator 129 can be used for reading a size indication provided at a corresponding location on the truing and drilling component 30.

Figure 3D:
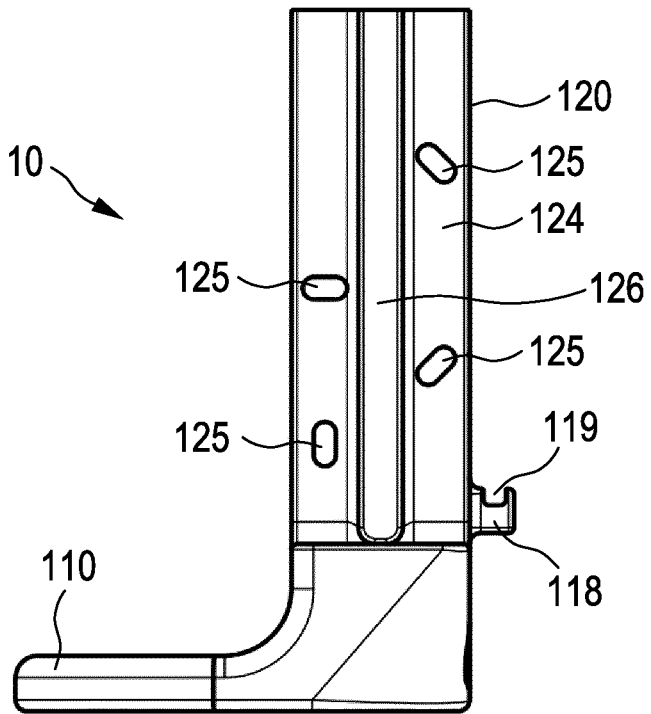

FIG. 3d shows a left side view of the guide component 10. The guide groove 126 runs along the lateral surface 124 in the direction of extent of the guide element 120, particularly in the center of the lateral surface 124. The knob 118 having the groove 119 on the top side thereof is further shown in the side view, by means of which the tensioning of the guide component 10 against the tensioning component 20 is performed. Two openings 125 each are provide on each side of the lateral surface 124, to the left and right of the guide groove 126. The openings 125 have different alignments in order to prevent incorrect locking by means of the locking pin 360. The orientations of the geometry of the openings 125 are designed according to the known method of "poka yoke."

Figure 3E:
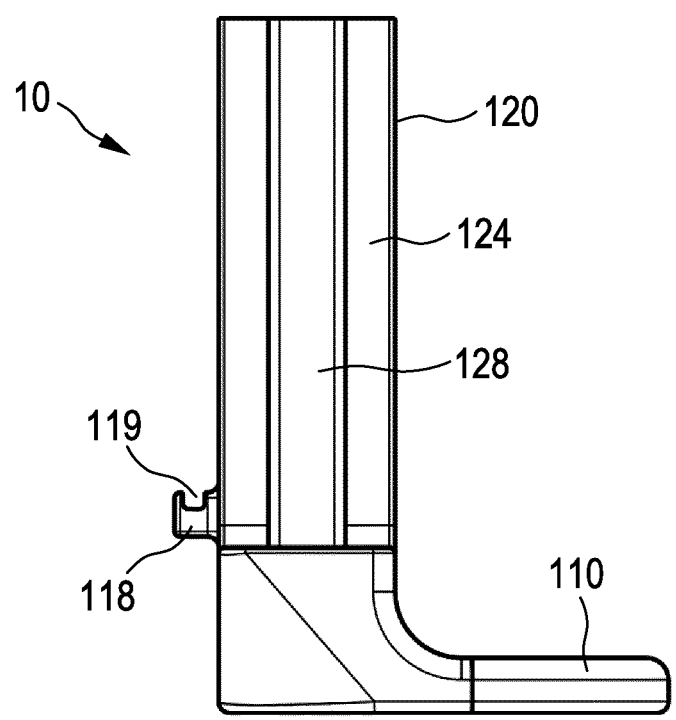

Finally, FIG. 3e shows a right side view of the guide component 10. The guide protrusion 128 of the side surface 124 runs along the lateral surface 124 in the direction of extent of the guide elements 120.

Figure 4A:
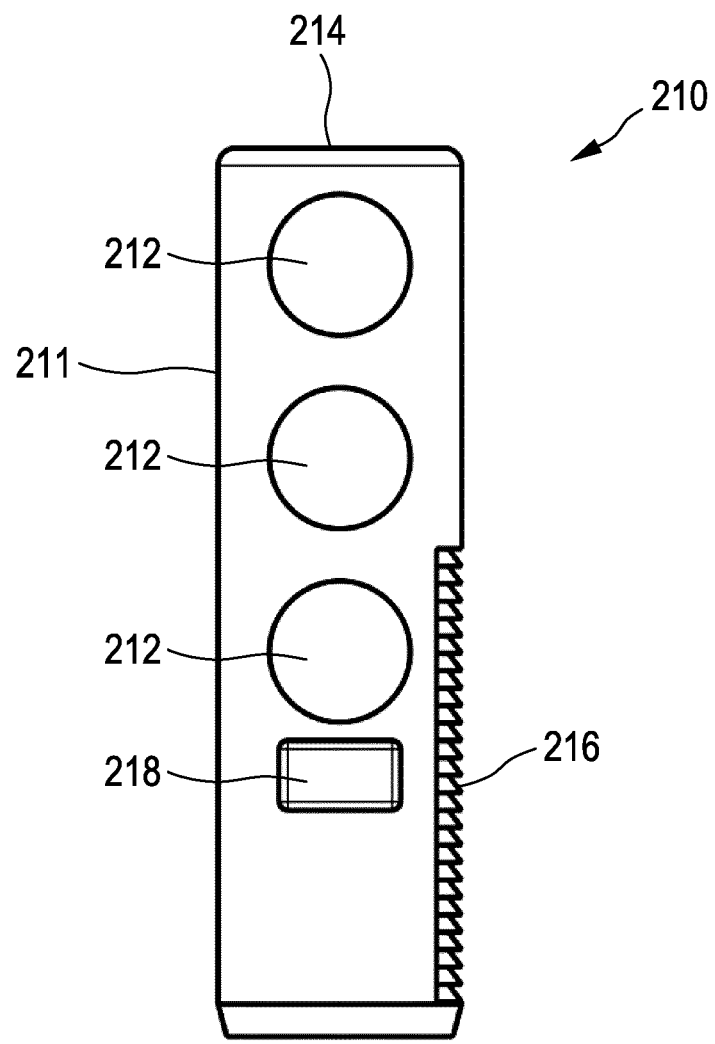
FIGS. 4a and 4b show schematic examples of two views of a tensioning cylinder according to one embodiment example.
Figure 4B:
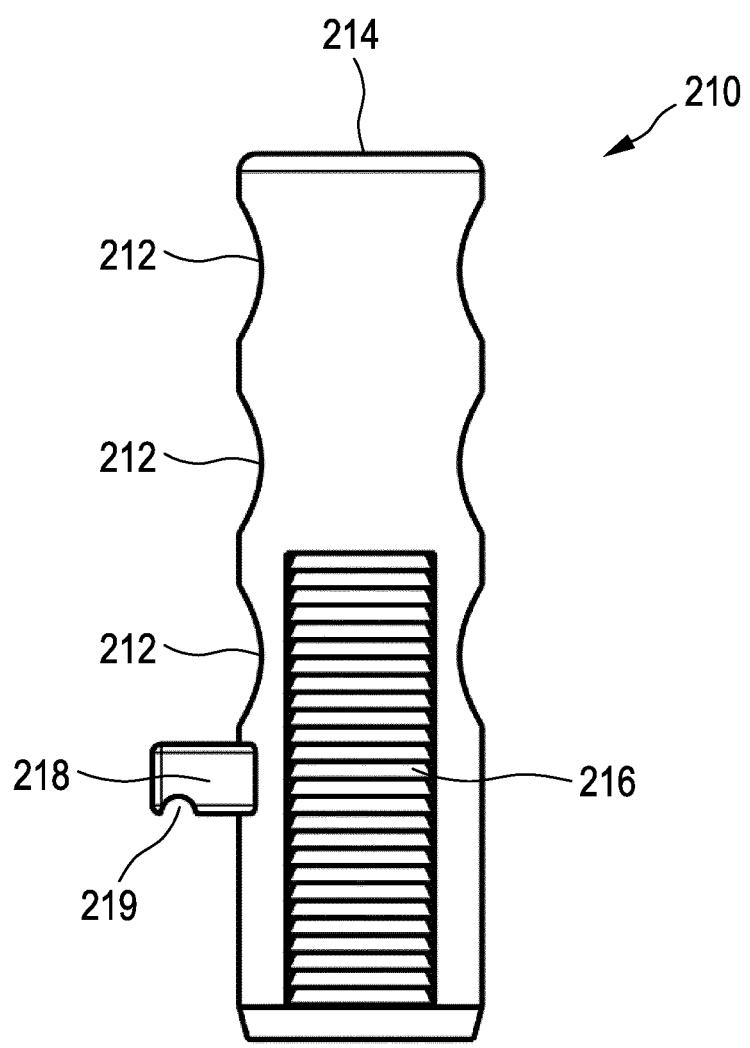

FIG. 4a shows a front view of an example of a tensioning cylinder 210 and FIG. 4b shows an example side view of the tensioning cylinder 210. The tensioning cylinder 210 substantially comprises a cylindrical pin 211. Three through holes 212 are provided transverse to the longitudinal direction of the cylindrical pin 211 in the present example. The through holes 212 each run parallel to each other through the center of the cylindrical pin 211. Various size settings of the surgery device 1 are made possible by means of the various through holes 212. In the present example, the middle through hole 212 is provided for a standard size. In the case of a particularly large or particularly small knee, the upper or lower through hole 212 can be used for fixing the surgery device 1 on the femur by means of the T-mount 250. In other examples, the tensioning cylinder 210 can also comprise only one or more than three through holes.

The tensioning cylinder 210 further comprises a cutout in the longitudinal direction 214. The cutout 214 preferably extends completely through the cylindrical pin 211. The cylindrical pin 211 can thus be described as a hollow cylinder. The cutout 214, however, can also extend through only part of the length of the cylindrical pin 211. The cutout 214 is particularly set up for preventing jamming due to bodily tissues or fluids.

The cylindrical pin 211 comprises a latching profile 216 on the cylindrical surface shown to the right in the image in FIG. 4a. The latching profile 216 is set up for latching with a corresponding latching profile of the tensioning lever 220 for enabling tensioning of the tensioning cylinder 210 relative to the tensioning lever and the guide component 10. In the present embodiment example, the latching profile 216 enables spacing the tensioning lever 220 and the tensioning cylinder 210 apart from each other, while displacement of each of the elements toward each other is blocked. In other embodiments, other latching profiles or other suitable mechanisms can be provided for enabling tensioning of the tensioning cylinder 210 and the tensioning lever 220.

The tensioning cylinder 210 further comprises the knob 218 on the front side thereof for tensioning, set up for tensioning relative to the corresponding knob 118 by means of a forceps, not shown. The knob 218 is thus a forceps protrusion.

Figure 5:
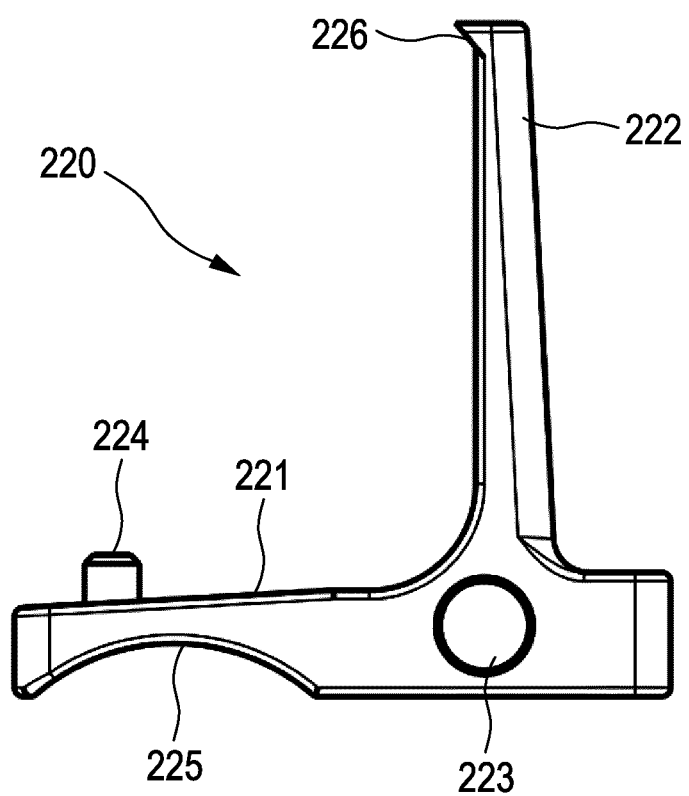
FIG. 5 shows a schematic example of a tensioning lever according to one embodiment example.

FIG. 5 shows a side view of the example of a tensioning lever 220. The tensioning lever 220 acts as a tensioning and releasing lever and comprises a first lever arm 221 and a second lever arm 222. The tensioning lever 220 is designed for rotating relative to a pivot point 223. The tensioning lever 220 is fastened to the guide component 10 at the pivot point 223 by means of the fastening screw 240. Displacing the first lever arm 221 thus brings about a corresponding rotational displacement of the second lever arm 222. The tensioning lever 220 further comprises a protruding cylinder 224 and a curved cutout 225 on the first lever arm 221 thereof. The cylinder 224 is implemented for securing the tensioning spring 230. The cutout 225 is opposite the cylinder 224 and enables the first lever arm 221 to be displaced in the direction of the cylinder 224 against the force of the tensioning spring 230 through the opening 116 of the base body 110. By displacing the first lever arm 221 upward in the drawing, the second lever arm 222 is displaced to the right in the drawing. A latching element 226 provided at one end of the second lever arm 222 is thus also displaced to the right. The latching element 226 is pretensioned against the latching element 216 of the tensioning cylinder 210 by the pretension of the tensioning spring 230. By pressing against the tensioning spring 230, the latching element 226 is relieved of pretension and the tensioning cylinder 210 can be released. In the side view, a groove 219 preventing a forceps used for tensioning from slipping off is shown on the bottom side of the knob 218.

Figure 6A:
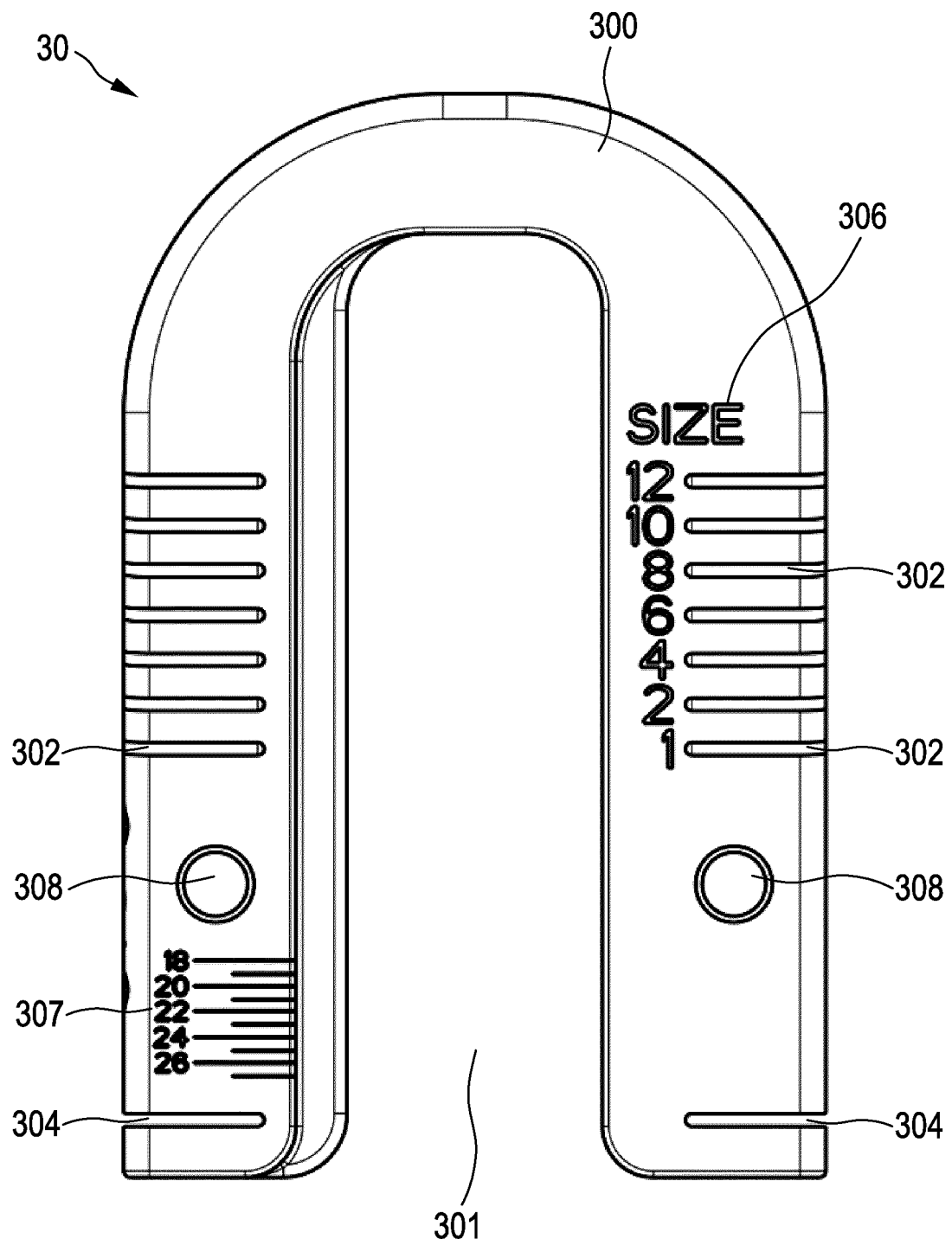
FIGS. 6a-6d show schematic examples of four views of a gauge fixture according to one embodiment example.
Figure 6B:
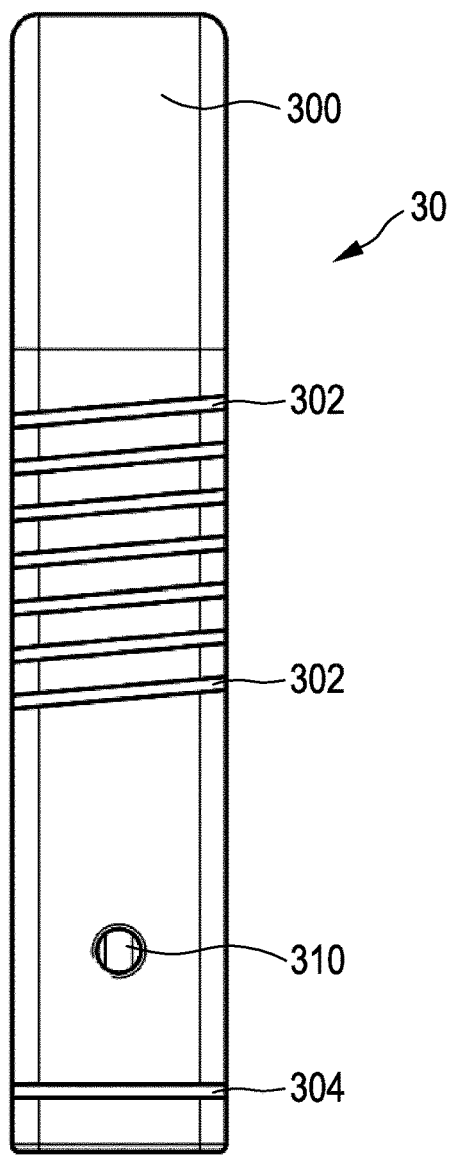

FIG. 6a shows a view of an example of a truing and drilling component 30 from the front and FIG. 6b shows a further view of the example of a truing and drilling component 30 from the side. Shown is a gauge fixture 300 placed on the guide element 120 and guided by the outer lateral surfaces 124. The gauge fixture 300 is implemented in the shape of an inverted U, so that the gauge fixture 300 can be placed on the guide component 10 due to a cut-out region 301. The gauge fixture 300 comprises a plurality of grooves 302 in the upper region thereof, set up for truing the upper femoral surface in the desired prosthesis size. A size indicator 306 printed on the front side defines which groove 302 is to be used for which prosthesis size. In the present example, the standard sizes 1, 2, 4, 6, 8, 10, and 12 are indicated.

In other examples of the gauge fixture 300, of course, other types and combinations of grooves 302 and size indications 306 are conceivable. The gauge fixture 300 further comprises a lower groove 304 in the lower region, set up for truing the lower femoral cut as well. The gauge fixture 300 further comprises one drill bushing 308 in each arm of the gauge fixture 300 for fastening the gauge fixture in the femur and defining the final drilling position or drilling the final prosthesis holes. The drill bushing 308 in the example is integral to the gauge fixture 300. The gauge fixture 300 thus comprises a material of sufficient hardness. In other examples, the drill bushing 308 can also be inserted, for example clamped, in the gauge fixture 300 in a known manner.

In the illustrated embodiment, the gauge fixture 300 comprises a millimeter scale 307 on the front side thereof. The millimeter scale 307 is referenced by a marking on the guide component.

In the side view shown in FIG. 6b, an adjustment thread 310 is also shown. By means of the adjusting thread 310, the adjusting screw 350 can be threaded in such that the gauge fixture 300 and the guide elements 120 are fixed to each other. The position of the truing and drilling component 30 relative to the guide component 10 can thereby be fixed. In the side view shown in FIG. 6b, it is evident that the upper grooves 302 do not run parallel to the lower grooves 304. In the example, the angle between the femoral end face and the upper grooves 302 is particularly 95°. In further examples of the gauge fixture 300, additional grooves, for example for performing diagonal cuts, can also be provided and the angles of the different grooves can be different.

Figure 6C:
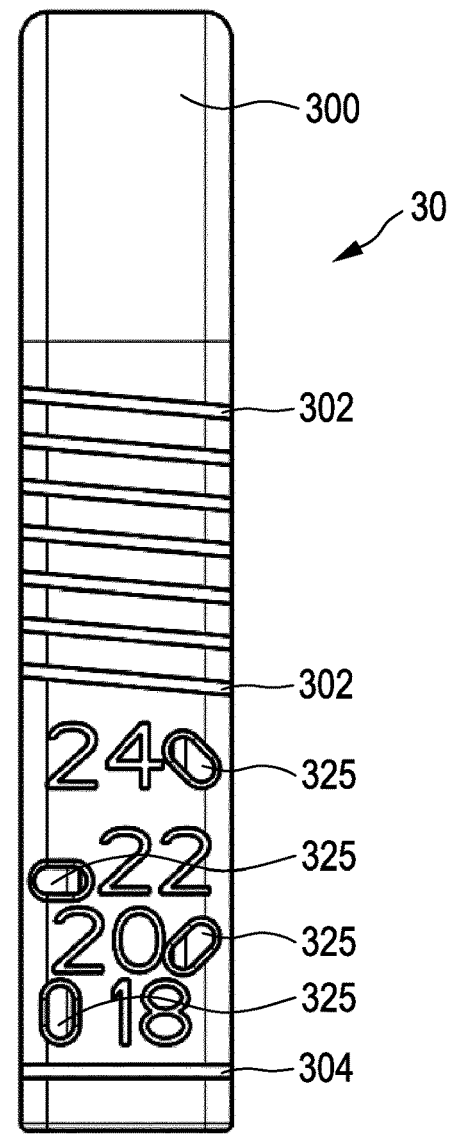

FIG. 6c shows a further side view of the gauge fixture 300 in which the openings 325 are shown for a locking pin 260 enabling positioning of the gauge fixture 300 at various heights above the guide component 10. Adjacent to each of the openings 325, a number shows a size relating to the opening, for example a size of the prosthesis, or a length indication in millimeters, or the like.

Figure 6D:
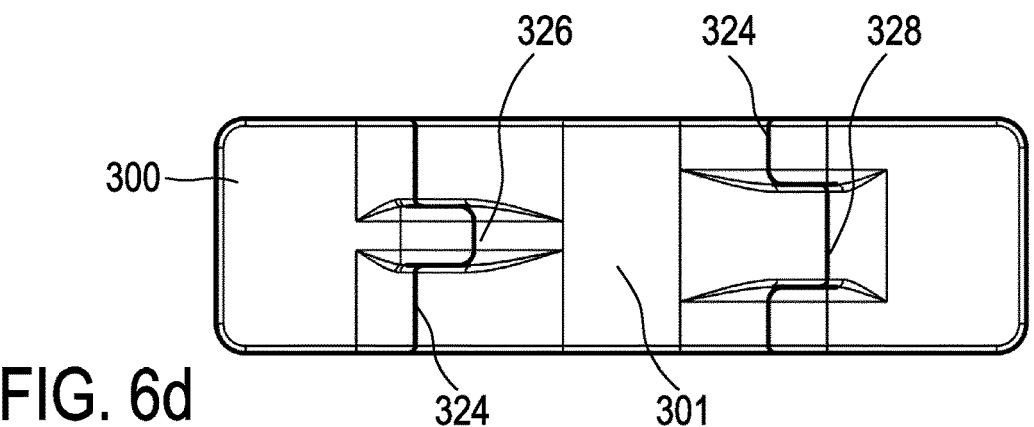

FIG. 6d shows a view from below of the gauge fixture 300. Opposing inner side walls 324 are set up for fitting to corresponding side walls 124 of the guide component 10. The cut-out region 301 in which the guide element 120 is received is indicated between the side walls 324. A protrusion 326 on the side wall 324 shown to the left in the figure is set up for being inserted in the guide groove 126 and for being guided therein. A groove or cutout 328 on the opposite lateral surface is set up for interacting with the guide protrusion 128 of the guide element 120.

FIG. 7a shows a side view of an embodiment example of the adjusting screw 350, and FIG. 7b shows a plan view of the adjusting screw 350 from the side of a screw head 354. The adjusting screw 350 comprises a thread 352 and the screw head 354 at one end. The screw head 354 is implemented such that said screw head is particularly easily actuated by hand. The circumference of the screw head 354 is not smooth, however, but rather comprises regular depressions 355. In other embodiment examples, of course, other screws can also be used. Alternative screws or fasting elements are preferably also implemented for being fixed by manual actuation and not by actuating by means of tools. A longitudinal knurl is particularly suitable to this end, for example.

FIG. 8 shows an example of a side view of a locking pin 360 providing a further option for how the truing and drilling component 30 can be fixed relative to the guide component 10. A first end 361 of the locking pin 360 is inserted through a locking opening 325 of the gauge fixture 300 and into a locking opening 125 on an outer lateral surface of the guide element 120. The locking pin 360 splits at a fork 362 and runs onward away from the first end 361 in a first arm 364 and a second arm 366. The locking pin is inserted into the locking opening 325 up to an edge 363. The distance between the first arm 364 and the second arm 366 in the region of the edge 363 is already greater than the diameter of the locking opening 325, so that the locking pin 360 is retained by the flexural stress between the two arms 364, 366 in the locking opening 325. A protrusion 365 for preventing undesired releasing and removing of the locking pin 360 from the locking opening 325 can be implemented both on the first arm 364 and on the second arm 366 in the region inserted into the locking opening 325. An eye 368 is further provided on an end opposite the first end 361. A chain can be attached to the eye 368 if needed and a loss of the locking pin in the open knee can thereby be prevented. The safety of the surgery is thereby further improved.

Figure 9A:
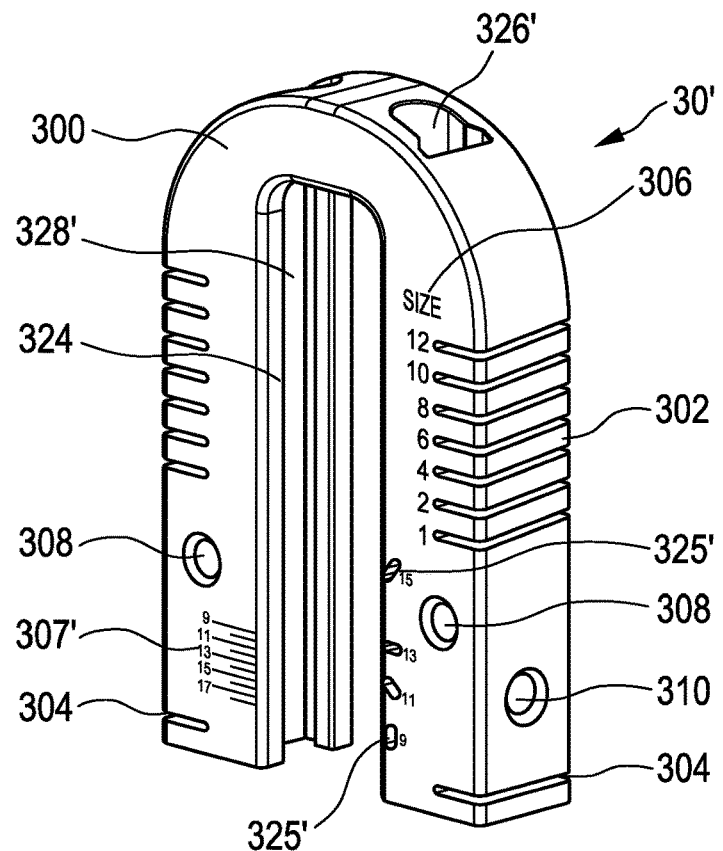
FIGS. 9a and 9b show schematic examples of two views of a further embodiment example of a gauge fixture.
Figure 9B:
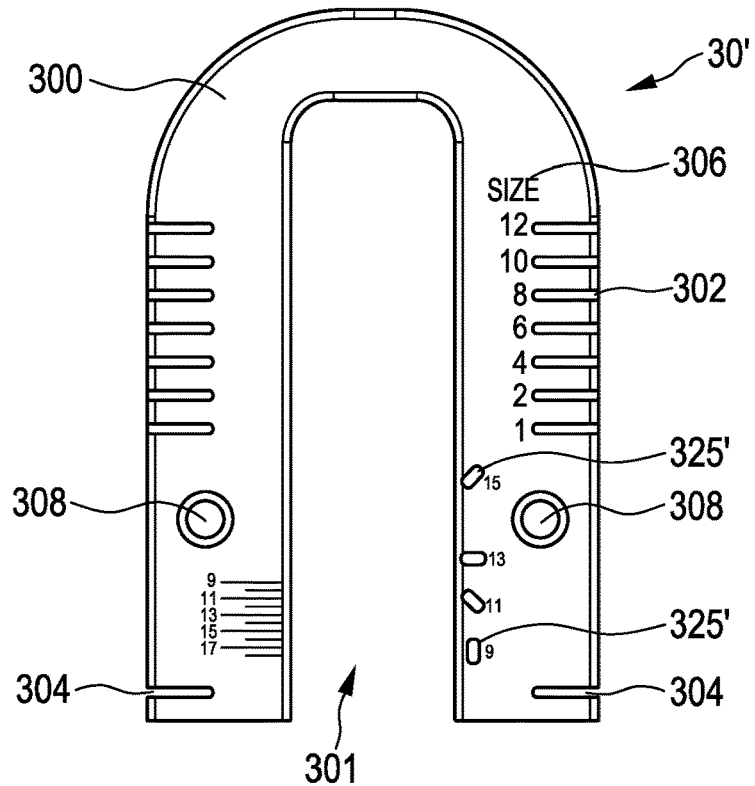

FIG. 9a and FIG. 9b show schematic examples of two views of a further embodiment example of a gauge fixture 30'. The gauge fixture 30' carries over substantial elements of the gauge fixture 30 shown as an example in FIGS. 6a through 6d. Identical reference numerals refer to identical elements are not described against below.

The gauge fixture 300 comprises openings 325' on the front side. The openings 325' fulfill the identical functionality as the openings 325, but are disposed on the front side in order to better ensure usability for surgeries on both the left and right knee. A locking pin 360 can be placed in the openings 325', for example for fixing the truing and drilling component 30'.

The guides 326' and 328' on the inner side wall 324 of the gauge fixture 300 differ further. In the example shown in FIG. 9, both of the guides 326' and 328' are implemented as dovetail guides.

Finally, the labeling 307' differs, wherein in FIG. 9 a so-called PE size, that is, a size of the prosthesis, is shown in place of the millimeter indications shown as an example in FIG. 6. In other embodiment examples, of course, other labels or no label whatsoever can also be used.

Figure 10:
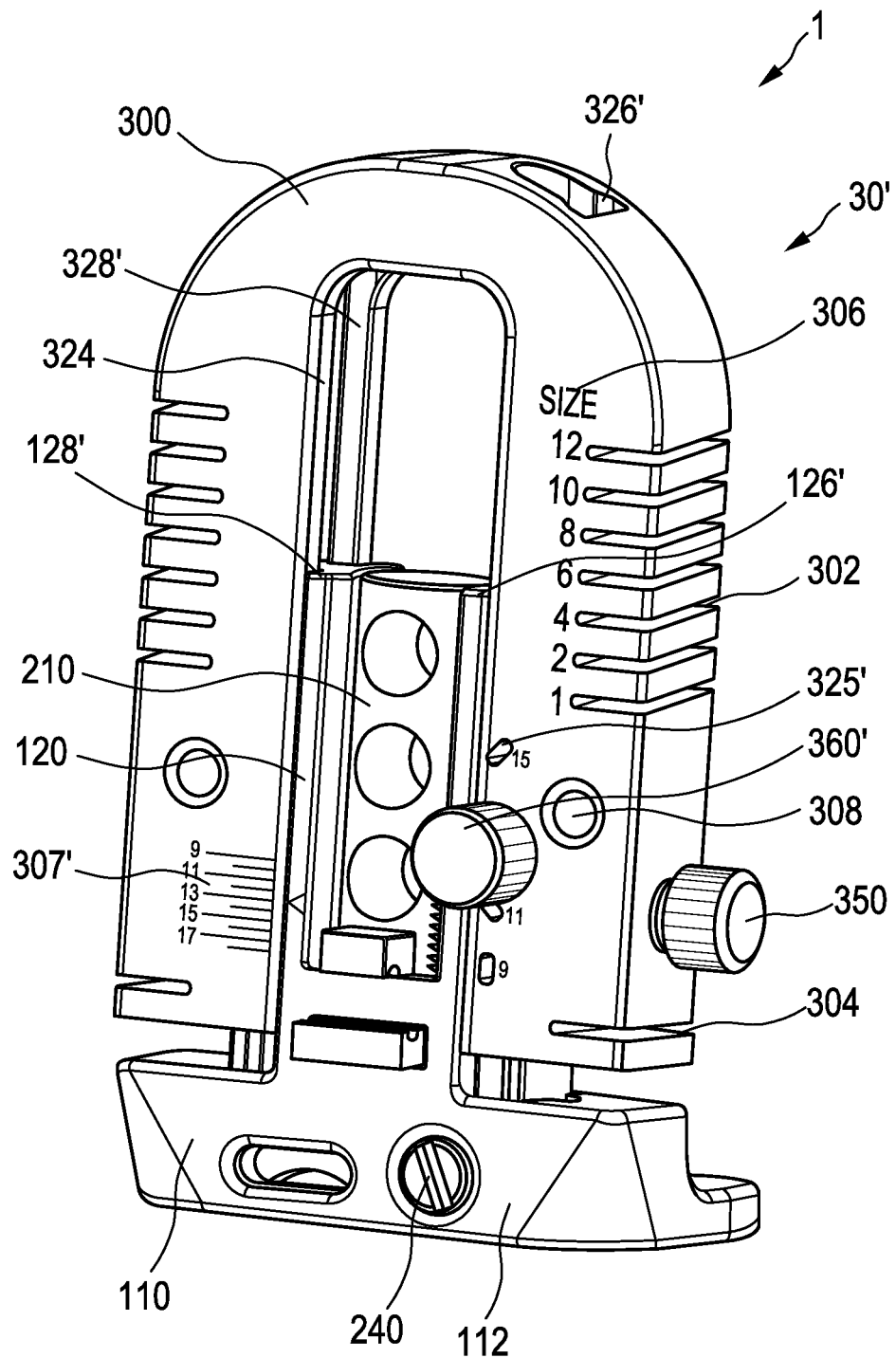
FIG. 10 shows a schematic example of a perspective view of a surgery device having the gauge fixture from FIG. 9.

FIG. 10 shows the truing and drilling component 30' shown in FIG. 9 in a position pushed onto and fixed to the guide elements 120 of the surgery device 1. In the present example, a locking pin 360' fixes the opening 325' associated with a prosthesis of size 13. The locking pin 360' comprises a round head having a transverse hole implemented therein in place of the eye 368, deviating from that shown in FIG. 8. The locking pin 360' comprises a longitudinal knurl about the round head. The guide elements comprise the counterparts of the dovetail guides 126' and 128' corresponding to the guides 326' and 328'.

Further advantages and improvements of the embodiment example of the device according to the invention in comparison with the prior art are described below.

A plurality of operationally independent functions are combined in one surgery device 1 by the device. Uniform tensioning of the ligaments can be achieved, accompanied by correct rotation/alignment of the femur and reproducible determining of the individually required size of prosthesis in a combined surgery device 1. The surgery device 1 enables truing of the upper and lower cut locations of the femur in a flexed position during the surgery as well as drilling of the two fastening holes for fastening the prosthesis in the femoral end face 4.

The angular displaceability of the tensioning cylinder 210 about the axis of rotation of the tensioning cylinder 210 is increased by the surgery device 1. By means of an installed force transmitting device, namely the T-mount 250, and by modifying the guiding of the tensioning cylinder 210 relative to the prior art, the angle of rotation of the tensioning cylinder 210 is increased.

The tensioning device mechanism implementing a tensioning of the tensioning lever 220 and of the tensioning cylinder 210 enables complete removal of the tensioning lever 220. Disinfectability is thereby increased and buildup of bodily fluids and/or tissue residues is prevented. The arrangement and geometry of the guide components and the tensioning component 20 allows displaceable parts to be relocated in the guide component 10, whereby unintended actuation of the mechanism, such as the tensioning lever 220, due to protruding control elements, is prevented.

The tensioning cylinder 210 is optimized in that a cutout 214 is provided in the longitudinal direction for receiving any foreign bodies, such as tissues, bones, cartilage, or the like in the tensioned state, and therefore jamming of the tensioning component 20 by material crushing/buildup is prevented.

The surgery device 1 combines a plurality of gaging and drilling devices, such as a gauge for the upper and lower femoral cuts and a gaging and drilling template for femoral holes, for simplifying the surgical process, for simplifying the surgical sequences, for shortening the time of surgery, and for optimizing the quality of surgery, by means of mechanically predetermined process sequences implemented by a gauge fixture 300 for pushing on and grooves 302 of the gauge for the upper femoral cut labeled with numerical values for determining the size of the prosthesis. The gauge fixture 300 can be continuously variably displaced and clamped or locked at predefined locations.

The gauge fixture 300 can be set by the adjusting screw 350. The setting device comprising the adjusting screw 350 further comprises a vernier scale for optimizing legibility, wherein the setting device is set up for setting the gauge fixture 300 in an analog manner. The setting mechanism is similar to that of a caliper gauge implemented having an adjusting screw 350, allowing implementation of continuously variable intermediate sizes depending on the surgical situation and the surgical anatomy of the patient.

A locking device of the gauge fixture 300 by the locking pin 360 enables a plurality of potential locking heights for adjusting the gauge fixture 300. For example, special spacings such as 18, 20, 22, 24 mm, relative to dimensions such as 18, 20, 22, 24 mm also specially determined in preceding surgical steps, for example, allow a plurality of potential locking heights of the gauge fixture 300. The locking is performed by the locking pin 360, wherein incorrect setting is prevented by special locking pin geometry. Each of the locking openings 325 can be implemented as rectangular elongated holes. The locking pin geometry comprises elongated holes in the gauge fixture and the guide elements 120, each hole rotated by 360° divided by the number of elongated holes. Numerical values for indicating the selected position are preferably provided on the outer surface of the gauge fixture 300. Said locking pin geometry is designed according to the known method of "poka yoke" for preventing unintentional malpositioning using geometric devices in this case.

The drill bushing 308 in the gauge fixture 300 is integrated in the gauge fixture 300 by means of sufficient base hardness of the material. Alternatively, the drill bushing can be implemented as a drill bushing insert and thereby clamped, pressed in, or otherwise fastened in the gauge fixture 300.

The base surface 111 of the base body 110 is optimized to the benefit of the surgery sequence. The geometry of the base surface 111 of the base body 110 is thereby modified to the benefit of preventing intrasurgical collisions with the cruciate ligament and/or other tissues. The geometry of the base surface 111 of the base body 110 is concave, for example, and comprises general elimination of sharp edges (radius, chamfer, or the like) of the contour for preventing cutting and scraping of tissues and bone.

In one example, the size of the base surface 111 of the base body 110 can be divided to the benefit of a surgery sequence and individual patient anatomy, that is, individual bone size. For example, the base body 110 can be divided into prosthesis sizes 1 through 6 and 8 through 12, possibly having overlapping sizes. The base surface 111 preferably makes plane-parallel and form-fit contact with the tibial end face 5.

The surgery device 1 and all components and elements can be made of different materials and optionally having different surface properties or coatings. All individual elements can be implemented as metal, as plastic, or as hybrids, optionally also in combination and in composite designs. Not all individual parts must be made of the same material, and combinations of different materials between different elements are also possible.

The surgery device 1 is conceived exclusively for optimizing the flexion gap occurring during the knee endoprosthesis surgery. Because uniform tensioning of the ligaments in a flexed position of the tibia to the femur is made possible, the femur can be aligned under balanced torque. If, in contrast, merely the parallelism of opposing tensioning surfaces in the flexed knee is used for aligning, then said essentially parallel forced position of the femur does not bring about uniform tensioning of the ligaments, but rather incorrect tensioning.

The surgery device according to the invention thus has the advantage, in comparison with said ligament alignment tensioned in parallel, that the femur can be aligned under balanced torque without the entire surgery process being implemented by using the integrated device.

Instead of the previous need for using individual device fixtures for the individual steps, the improvement over the prior art lies in recognizing the interrelation between the fixed hole spacing from the bottom edge of the device while simultaneously truing the size of the prosthesis by locking the size by means of a locking pin 360 or clamping screw 350 and integrating in a single device. In comparison with known device, the device 1 according to the invention having the single combined truing and drilling component 30 enables the steps of determining the size of the prosthesis and the drilled holes for the associated saw block to be implemented together in one unit when generating the flexion gap.

The invention claimed is:

1. A surgery device for operating on a human knee, the surgery device comprising:
   a guide component and a tensioning component, and
   a truing and drilling component for truing and drilling a femoral end face,
   wherein the guide component comprises a base body having a base surface for disposing on a tibial end face and guide elements extending from the base surface,
   wherein the tensioning component is configured to tension the guide component such that ligaments of the knee are uniformly tensioned in a flexed state of the knee,
   wherein the truing and drilling component is configured to be pushed onto the guide elements and fixed at various positions relative to the base surface,
   wherein the tensioning component comprises a tensioning cylinder and a tensioning lever,
   wherein the tensioning cylinder is guided by the guide elements along a longitudinal axis of the tensioning cylinder, and
   wherein the tensioning lever is configured to tension the tensioning cylinder relative to the base body.

2. The surgery device according to claim 1, wherein the tensioning cylinder comprises a cutout in a longitudinal direction.

3. The surgery device according to claim 2, wherein the cutout is a recess or a through hole.

4. The surgery device according to claim 1, wherein the tensioning lever comprises a first arm, a second arm, and a pivot point between said first and second arms, wherein the tensioning lever is configured such that the second arm is tensioned against the tensioning cylinder by a pretensioning of the first arm.

5. The surgery device according to claim 4, wherein the base body comprises an opening for actuating the tensioning lever on a lateral surface thereof.

6. The surgery device according to claim 1, wherein the base body comprises a cutout on the base surface for receiving the tensioning lever.

7. The surgery device according to claim 1, wherein the guide component comprises two guide elements spaced apart from each other by a distance and extending in a same direction as each other from the base body, wherein the two guide elements each comprise one inner lateral surface facing toward the other one of the guide elements of the two guide elements and one outer surface opposite the inner lateral surface.

8. The surgery device according to claim 7, wherein one of the outer surfaces of the two guide elements comprises a recess and the other one of the outer surfaces of the two guide elements comprises a protrusion in a direction of extent of the guide elements for guiding the truing and drilling component.

9. The surgery device according to claim 7, wherein the outer surfaces of the guide elements form a dovetail guide for guiding the truing and drilling component.

10. A surgery device for operating on a human knee, the surgery device comprising:
    a guide component and a tensioning component, and
    a truing and drilling component for truing and drilling a femoral end face,
    wherein the guide component comprises a base body having a base surface for disposing on a tibial end face and guide elements extending from the base surface,
    wherein the tensioning component is configured to tension the guide component such that ligaments of the knee are uniformly tensioned in a flexed state of the knee,
    wherein the truing and drilling component is configured to be pushed onto the guide elements and fixed at various positions relative to the base surface, and
    wherein the truing and drilling component comprises a gauge fixture, wherein the gauge fixture comprises at least one groove for an upper femoral cut.

11. The surgery device according to claim 10, wherein the gauge fixture comprises a plurality of pass-through openings and a guide element comprises a plurality of cutouts, wherein each of the pass-through openings is associated and has a same orientation with a corresponding one of the plurality of cutouts, and wherein the pass-through openings are different from each other and have orientations different from each other.

12. The surgery device according to claim 11, wherein the pass-through openings are disposed on a front side of the gauge fixture, wherein the front side of the gauge fixture is configured to face away from the femoral end face when the surgery device is in use.

13. The surgery device according to claim 12, wherein the gauge fixture comprises a millimeter scale on the front side thereof referenced by a marking on the guide component.

14. The surgery device according to claim 10, wherein the gauge fixture is configured to be set at a variable height position relative to the base surface by a setting element.

15. The surgery device according to claim 14, wherein the setting element is a clamping screw.

16. The surgery device according to claim 10, wherein the gauge fixture comprises two drill bushings configured to drill femoral prosthesis holes, wherein the two drill bushings are integrated in the gauge fixture or are drill bushing inserts.

17. A surgery device for operating on a human knee, the surgery device comprising:
    a guide component and a tensioning component, and
    a truing and drilling component for truing and drilling a femoral end face,
    wherein the guide component comprises a base body having a base surface for disposing on a tibial end face and guide elements extending from the base surface,
    wherein the tensioning component is configured to tension the guide component such that ligaments of the knee are uniformly tensioned in a flexed state of the knee,
    wherein the truing and drilling component is configured to be pushed onto the guide elements and fixed at various positions relative to the base surface, wherein the guide component comprises two guide elements spaced apart from each other by a distance and extending in a same direction as each other from the base body, wherein the two guide elements each comprise one inner lateral surface facing toward the other one of the guide elements of the two guide elements and one outer surface opposite the inner lateral surface, wherein each of the inner lateral surfaces comprises a concave cylindrical shape such that the two inner lateral surfaces define a cylindrical guide by the distance therebetween.

18. The surgery device according to claim 17, wherein one of the outer surfaces of the two guide elements comprises a recess and the other one of the outer surfaces of the two guide elements comprises a protrusion in a direction of extent of the guide elements for guiding the truing and drilling component.

19. The surgery device according to claim 17, wherein the outer surfaces of the guide elements form a dovetail guide for guiding the truing and drilling component.

* * * * *